(12) United States Patent
Gleave et al.

(10) Patent No.: US 7,534,773 B1
(45) Date of Patent: May 19, 2009

(54) TRPM-2 ANTISENSE THERAPY

(75) Inventors: Martin Gleave, Vancouver (CA); Paul S. Rennie, Richmond (CA); Hideaki Miyake, Vancouver (CA); Colleen Nelson, Surrey (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/913,325

(22) PCT Filed: Feb. 25, 2000

(86) PCT No.: PCT/US00/04875

§ 371 (c)(1),
(2), (4) Date: Aug. 10, 2001

(87) PCT Pub. No.: WO00/49937

PCT Pub. Date: Aug. 31, 2000

Related U.S. Application Data

(60) Provisional application No. 60/121,726, filed on Feb. 26, 1999.

(51) Int. Cl.
*A61K 31/70* (2006.01)
*C07H 21/04* (2006.01)

(52) U.S. Cl. .................................. 514/44; 536/24.5

(58) Field of Classification Search .................. 514/44; 536/24.5
See application file for complete search history.

(56) References Cited

U.S. PATENT DOCUMENTS

| | | | |
|---|---|---|---|
| 5,563,255 A * | 10/1996 | Monia et al. | 536/24.31 |
| 5,646,042 A | 7/1997 | Stinchcomb et al. | |
| 5,789,389 A | 8/1998 | Tarasewicz et al. | |
| 5,801,154 A * | 9/1998 | Baracchini et al. | 514/44 |
| 5,929,040 A | 7/1999 | Werther et al. | |
| 5,998,148 A | 12/1999 | Bennett et al. | |
| 6,172,216 B1 | 1/2001 | Bennett et al. | |
| 6,335,194 B1 | 1/2002 | Bennett et al. | |
| 6,383,808 B1 | 5/2002 | Monia et al. | 435/375 |

FOREIGN PATENT DOCUMENTS

| WO | WO 00/49937 | 8/2000 |
|---|---|---|
| WO | WO 01/46455 A2 | 6/2001 |
| WO | WO 02/22635 A1 | 3/2002 |
| WO | WO 03/062421 A1 | 7/2003 |
| WO | WO 03/072591 A1 | 9/2003 |

OTHER PUBLICATIONS

Agrawal et al. Molecular Medicine Today, 2000, vol. 6, p. 72-81.*
Branch TIBS 1998, vol. 23, p. 45-50.*
Jen et al. Stem Cells 2000, vol. 18, p. 307-319.*
Crooke, Antisense Research and Application, Chapter 1, Springer-Verlag, New York. 1998.*
Opalinska et al. Nature Reviews Drug Discovery, 2002, vol. 1, p. 503-514.*
Raghavan et al. European Journal of Cancer 1997, vol. 33, pp. 566-574.*
Buttyan et al., "Induction of the TRPM-2 Gene in Cells Undergoing Programmed Death" *Molecular and Cellular Biology* Aug. 1989, vol. 9, No. 8, pp. 3473-3481.
Millar et al., "Localization of mRNAs by in-situ hybridization to the residual body at stages IX-X of the cycle of the rat seminiferous epithelium: fact or artefact?" *International Journal of Andrology*, 17:149-160.
Darby et al., "Vascular Expression of Clusterin in Experimental Cyclosporine Nephrotoxicity" *Exp Nephrol* 1995; 3:234-239.
Milner et al., "Selecting effective antisense reagents on combinatorial oligonucleotide arrays" *Nature Biotechnology* vol. 15, Jun. 1997, pp. 537-541.
Sensibar et al., "Prevention of Cell Death Induced by Tumor Necrosis Factor alpha in LNCaP Cells by Overexpression of Sulfated Glycoprotein-2 (Clusterin)," *Cancer Research*, Jun. 1, 1995, vol. 55, pp. 2431-2437.
Miyake et al., "Testosterone-repressed Prostate Message-2 Is an Antiapoptotic Gene Involved in Progression to Androgen Independence in Prostate Cancer", *Cancer Research 60*, Jan. 1, 2000, pp. 170-176.
Yang et al., "Nuclear clusterin/XIP8, an x-ray-induced Ku70-binding protein that signals cell death", *Proc. Nat'l. Acad. Sci. USA*, vol. 97, Issue 11, pp. 5907-5912, May 23, 2000.
Benner, et al., "Combination of Antisense Oligonucleotide and Low-Dose Chemotherapy in Hematological Malignancies", *Journal of Pharmacological and Toxicological Method*, 37:229-235 (1997).
Kadomatsu, et al, "Expression of sulfated glycoprotein 2 is associated with carcinogenesis induced by N-nitroso-N-methylurea in rat prostate and seminal vesicle", *Cancer Res* Apr. 1, 1993, 53(7):1480-1483.
Kyprianou, et al., "bcl-2 over-expression delays radiation-induced apoptosis without affecting the clonogenic survival of human prostate cancer cells.", *Int J Cancer*, Jan. 27, 1997, 70(3):341-348.
Wright, et al., "A ribonucleotide reductase inhibitor, MDL 101,731, induces apoptosis and elevates TRPM-2 mRNA levels in human prostate tumor xenografts.", *Exp Cell Res*, Jan. 10, 1996, 222(1):54-60.

(Continued)

*Primary Examiner*—Tracy Vivlemore
(74) *Attorney, Agent, or Firm*—Marina Larson & Associates, LLC

(57) ABSTRACT

Antisense therapy which reduces the expression of TRPM-2 provides therapeutic benefits in the treatment of cancer for example prostate cancer and renal cell cancer. Antisense TRPM-2 ODN treatment of prostatic tumor cells in vivo is effective for delaying the onset of androgen independence and can be used in combination with androgen-withdrawal to induce apoptotic cell death of prostatic tumor cells in the individual. Combined use of antisense TRPM-2 and taxanes synergistically enhances cytotoxic chemosensitivity of androgen-independent prostate cancer. Radiation sensitivity is also enhanced when cells expressing TRPM-2 are treated with antisense TRPM-2 ODN. Thus, the antisense TRPM-2 ODNs can be used to enhance hormone sensitivity, chemosensitivity and radiation sensitivity of a variety of cancer types in which expression of TRPM-2 has been observed.

12 Claims, 15 Drawing Sheets

OTHER PUBLICATIONS

Bruchovsky, et al., "Control of tumor progression by maintenance of apoptosis", *Prostate Suppl.*, 1996, 6:13-21.

Nör et al.; Up-Regulation of Bcl-2 in Microvascular Endothelial Cells Enhanced Intratumoral Angiogenesis and Accelerates Tumor Growth; Cancer Research; vol. 61; Mar. 1, 2001; 2183-2188.

Kirby et al.; Bartonella-Associated Endothelial Proliferation Depends on Inhibition of Apoptosis: PNAS; vol. 99, No. 7; Apr. 2, 2002; 4656-4661.

Cox et al.; Angiogenesis and Non-Small Cell Lung Cancer; vol. 27, 2000; 81-100.

Tran et al.; A Role for Survivin in Chemoresistance of Endothelial Cells Mediated by VEGF; PNAS; vol. 99, No. 7; Apr. 2, 2002; 4349-4354.

Nör et al.; Engineering and Characterization of Functional Human Microvessels in Immunodeficient Mice; Laboratory Investigation; vol. 81, No. 4; Apr. 2001; 453-463.

Boral et al.; Clinical Evaluation of Biologically Targeted Drugs: Obstacles and Opportunities; Cancer Chemother Pharmacol; vol. 42; 1998; S3-S21.

Zwain et al.; Clusterin Protects Granulosa Cells from Apoptotic Cell Death During Follicular Atresia; Experimental Cell Research; vol. 257; 2000; 101-110.

Lee et al.; In Vitro Models of Prostate Apoptosis: Clusterin as an Antiapopotic Mediator; The Prostate Supplement; vol. 9; 2000; 21-24.

Genta Incorporated; New Data Reaffirm Genta's Molecular Target as Critical Factor for Enhancing Anticancer Treatment; www.genta.com; 2001.

Gleave et al., Use of Antisense Oligonucleotides Targeting the Antiapoptotic Gene, Clusterin/Testosterone-Repressed Prostate Message 2, to Enhance Androgen Sensitivity and Chemosensitivity in Prostate Cancer, 2001, pp. 39-49, Publisher: Elsevier Science Inc.

Gleave et al., Antisense therapy: Current status in prostate cancer and other malignanices, Cancer and Metastasis Reviews, 2002 pp. 79-92, vol. 21, Publisher: Kluwer Academic Publishers.

Gleave et al., Targeting anti-apoptotic genes unregulated by androgen withdrawal using antisense oligonucleotides to enhance androgen—and chemo-sensitivity in prostate cancer, Investigational New Drugs, 2002, pp. 145-158, vol. 20, Publisher: Kluwer Academic Publishers.

Gleave et al., Antisense Targets to Enhance Hormone and Cytotoxic Therapies in Advanced Prostate Cancer, Current Drug Targets, 2003, pp. 209-221, vol. 4.

Jones et al., Molecules in focus Clusterin, The International Journal of Biochemistry and Cell Biology, 2002, pp. 427-431, vol. 34.

Miyake et al., Novel therapeutic strategy for advanced prostate cancer using antisense oligodeoxynucleotides targeting antiapoptotic genes upregulated after androgen withdrawal to delay androgen-independent progression and enhance chemosensitivity, International Journal of Urology, 2001, pp. 337-349, vol. 8.

Miyake et al., Synergistic Chemsensitization and Inhibition of Tumor Growth and Metastasis by the Antisense Oligodeoxynucleotide Targeting Clusterin Gene in a Human Bladder Cancer Model [1], Clinical Cancer Research, Dec. 2001, pp. 4245-4251, vol. 7.

Miyake et al., Antisenst TRPM-2 Oligodeoxynucleotides Chemosensitize Human Androgen-independent PC-3 Prostate Cancer Cells Both in Vitro and in Vivo [1], Clinical Cancer Research, May 2000, pp. 1655-1663, vol. 6.

Rosenberg et al., Clusterin: Physiologic and Pathophysiologic Considerations, International Journal of Biochemistry, 1995, pp. 633-645, vol. 27, No. 7, Publisher: Elsevier Scienct Ltd.

Wilson et al., Clusterin is a secreted mammalian chaperone, Frontlines, Mar. 2000, pp. 95-98.

Wong et al., Molecular characterization of human TRPM-2/clusterin, a gene associated with sperm maturation, apoptosis and neurodegeneration, European Journal of Biochemistry, 1994, pp. 917-925, vol. 227.

Zangemeister-Wittke et al., A Novel Bispecific Antisense Oligonucleotide Inhibiting Both *bcl-2* and *bcl-xL* Expression Efficiently Induces Apoptosis in Tumor Cells, Clinical Cancer Research, Jun. 2000, pp. 2547-2555, vol. 6.

Zellweger et al., Antitumor Activity of Antisense Clusterin Oligonucleotides is Improved in Vitro and in Vivo by Incorporation of 2'-O-(2-Methoxy)Ethyl Chemistry, The Journal of Pharmacology and Experimental Therapeutics, Feb. 2001, pp. 934-940, vol. 298, No. 3.

Zellweger et al., Chemosensitization of Human Renal Cell Cancer Using Antisense Oligonucleotides Targeting the Antiapoptotic Gene Clusterin [1], The Prostate Centre, 2001, pp. 360-367, vol. 3, No. 4, Publisher: Nature Publishing Group.

* cited by examiner

TRPM-2 ANTISENSE THERAPY

This application is a Section 371 national phase application based upon International Patent Application No. PCT/US00/04875, filed Feb. 25, 2000, and claims the benefit of U.S. Provisional Application No. 60/121,726, filed Feb. 26, 1999, which is incorporated herein by reference.

BACKGROUND OF THE INVENTION

This application relates to antisense treatments for cancer making use of an antisense oligonucleotide that binds to testosterone-repressed prostate message-2 (TRPM-2).

Prostate cancer is the most common cancer that affects men, and the second leading cause of cancer deaths in men in the Western world. Because prostate cancer is an androgen-sensitive tumor, androgen withdrawal, for example via castration, is utilized in some therapeutic regimens for patients with advanced prostate cancer. Androgen withdrawal leads to extensive apoptosis in the prostate tumor, and hence to a regression of the disease. However, castration-induced apoptosis is not complete, and a progression of surviving tumor cells to androgen-independence ultimately occurs. This progression is the main obstacle to improving survival and quality of life, and efforts have therefore been made to target androgen-independent cells. These efforts have focused on non-hormonal therapies targeted against androgen-independent tumor cells (Yagoda et al., *Cancer* 71 (Supp. 3): 1098-1109 (1993); Oh et al., *J. Urol.* 60:1220-1229 (1998)), however, so far no non-hormonal agent has improved survival. Alternative approaches are therefore indicated.

It has been observed that numerous proteins are expressed in increased amounts by prostate tumor cells following androgen withdrawal. At least some of these proteins are assumed to be associated with the observed apoptotic cell death which is observed upon androgen withdrawal. (Raffo et al., *Cancer Res.,*: 4448-4445 (1995); Krajewska et al., *Am. J. Pathol.* 148:1567-1576 (1996); McDonnell et al., *Cancer Res.* 52:6940-6944 (1992)). The functions of many of the proteins, however, is not clearly understood. TRPM-2 (also known as sulfated glycoprotein-2 (SGP-2) or clusterin) is within this latter category.

TRPM-2 is a ubiquitous protein, with a diverse range of proposed activities. In prostate epithelial cell, expression of TRPM-2 increases immediately following castration, reaching peak levels in rat prostate cells at 3 to 4 days post castration, coincident with the onset of massive cell death. These results have led some researchers to the conclusion that TRPM-2 is a marker for cell death, and a promoter of apoptosis. On the other hand, the observation that Sertoli cells and some epithelial cells express high levels of TRPM-2 without increased levels of cell death, raises questions as to whether this conclusion is correct.

Sensibar et al., *Cancer Research* 55:2431-2437 (1995) reported on in vitro experiments performed to more clearly elucidate the role of TRPM-2 in prostatic cell death. They utilized LNCaP cells transfected with a gene encoding TRPM-2 and observed whether expression of this protein altered the effects of tumor necrosis factor α (TNFα), to which LNCaP cells are very sensitive, with cell death normally occurring within about 12 hours. Treatment of the transfected LNCaP cells with TNFα was shown to result in a transient increase in TRPM-2 levels for a period of a few hours, but these levels had dissipated by the time DNA fragmentation preceeding cell death was observed. Using an antisense molecule corresponding to the bases 1-21 of the TRPM-2 sequence, but not other TRPM-2 antisense oligonucleotides, resulted in a substantial reduction in expression of TRPM-2, and an increase in apoptotic cell death in LNCaP cells exposed to TNFα. This led Sensibar et al. to the hypothesis that overexpression of TRPM-2 could protect cells from the cytotoxic effect of TNF, and that TRPM-2 depiction is responsible for the onset of cell death, although the mechanism of action remains unclear.

While Sensibar et al. provides information about the possible role of TRPM-2, it nevertheless discloses results from only a model system in which expression of TRPM-2 is based on a transfected gene. Furthermore, expression levels of TRPM-2 is very low or absent in LNCaP cells grown in other labs. The situation which results in vivo when prostate tumor cells are subjected to androgen withdrawal is far more complex, with numerous proteins changing expression levels as a result. Thus, it is not possible from the Sensibar et al. data to predict whether TRPM-2 would perform the same function when present in combination with other proteins, or whether changes in levels of TRPM-2 following androgen withdrawal in vivo could provide any therapeutic benefits. Indeed, the fact that TRPM-2 is expressed in substantial quantities in prostatic tumor cells at various stages following androgen withdrawal, including stages where significant apoptotic cell death is occurring suggests that role of TRPM-2 in vivo may be more complicated. Thus, while the art provides data concerning certain aspects of apoptotic cell death in prostatic tumor cells, it offers neither a teaching or a suggestion of a methodology to provide a delay in the onset of androgen-independence.

It is an object of the present invention to provide such a method.

It is a further object of the present invention to provide therapeutic antisense molecules for delaying the onset of androgen independence in prostatic tumor cells.

It is an additional object of the present invention to provide a method for enhancing the chemosensitivity or radiation sensitivity of cancer cells from a cancer that expresses TRPM-2.

It is a further object of the present invention to provide therapeutic antisense molecules for inhibiting expression of TRPM-2.

SUMMARY OF THE INVENTION

In accordance with the present invention, it has now been determined that antisense therapy which reduces the expression of TRPM-2 provides therapeutic benefits in the treatment of cancer. In particular, such antisense therapy can be applied in treatment of prostate cancer and renal cell cancer.

Addition of antisense TRPM-2 oligodeoxynucleotide (ODN) to prostatic tumor cells in vivo is effective for delaying the onset of androgen independence. Thus, in one aspect, the invention provides a method for treating prostate cancer in an individual suffering from prostate cancer, comprising the steps of initiating androgen-withdrawal to induce apoptotic cell death of prostatic tumor cells in the individual, and administering to the individual a composition effective to inhibit expression of TRPM-2 by the tumor cells, thereby delaying the progression of prostatic tumor cells to an androgen-independent state in an individual. Furthermore, combined use of antisense TRPM-2 plus cytotoxic chemotherapy (e.g. taxanes) synergistically enhances chemosensitivity in hormone refractory prostate cancer. In another aspect of the invention, a second antisense ODN which inhibits expression of an anti-apoptotic protein other than TRPM-2 is administered along with the antisense TRPM-2 ODN.

It has also been found that antisense TRPM-2 has beneficial effects for other cancer types. Specifically, antisense TRPM-2 ODN enhances chemosensitivity in human Renal cell cancer, a normally chemoresistant disease with no active chemotherapeutic agent having an objective response rate higher than 10%. Radiation sensitivity is also enhanced when cells expressing TRPM-2 are treated with antisense TRPM-2 ODN. Thus, the antisense TRPM-2 ODNs can be used to treat a variety of cancer types in which expression of TRPM-2 has been observed.

BRIEF DESCRIPTION OF THE FIGURES

FIGS. 12A and 12B show the increased sensitivity of Shionogi tumor cells to chemotherapy agents paclitaxel and mitoxanthrone when administered with antisense TRPM-2 ODN.

DETAILED DESCRIPTION OF THE INVENTION

Figure 1:
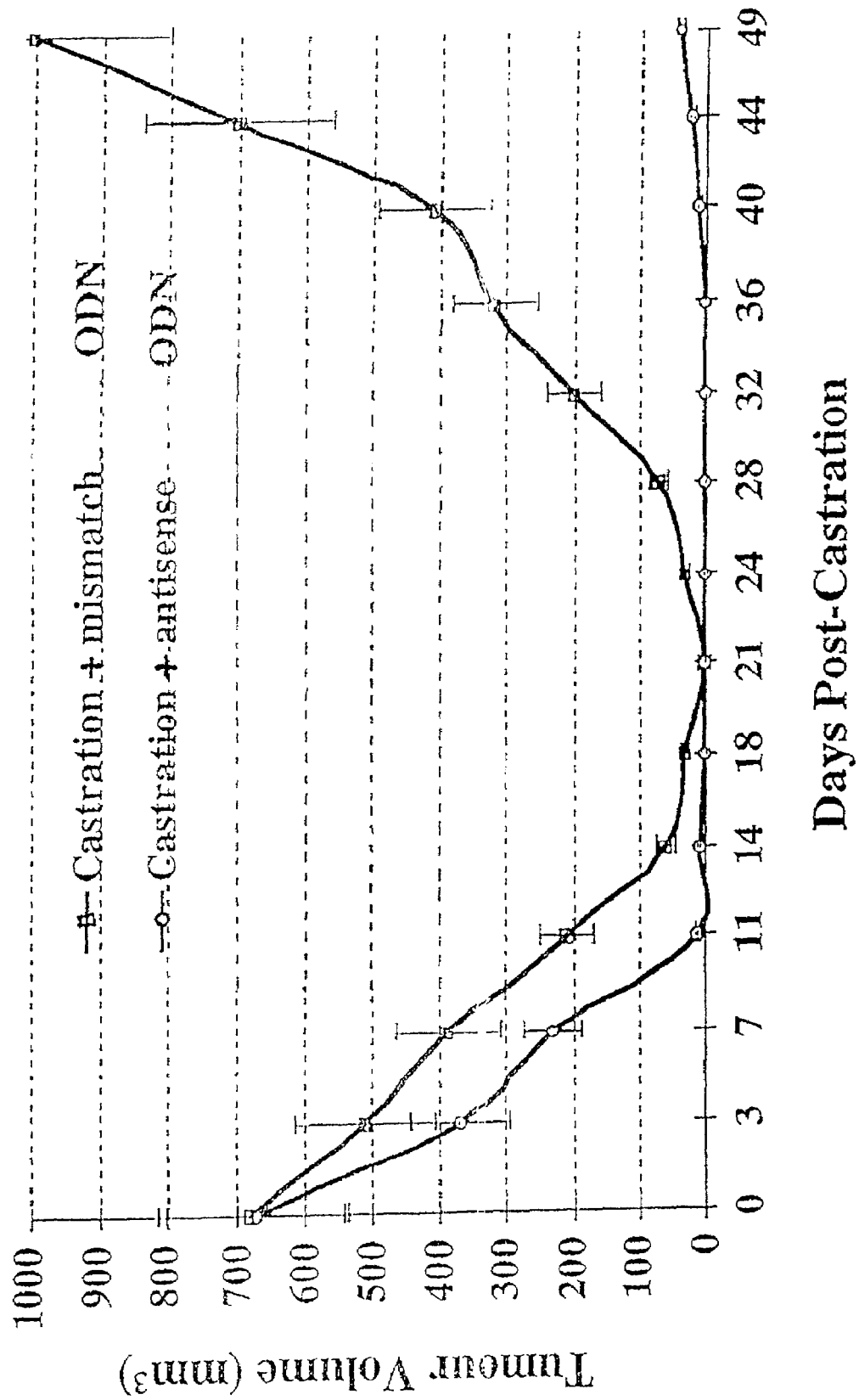
FIG. 1 shows the delay in onset of androgen-independence which is achieved using an antisense TRPM-2 ODN.

The present invention relates to antisense TRPM-2 ODNs and to the use of these compositions in the treatment of cancer. The invention can be applied in the treatment of cancers where the cancer cells express TRPM-2. Three significant classes of cancer cells which express TRPM-2 are prostate cancer cells, human renal cell cancer (RCC) cells and some breast cancer cells.

In one embodiment, the present invention provides a method for enhancing castration-induced tumor cell death and delaying the progression of prostatic tumor cells to androgen independence; a therapeutic method for the treatment of individuals, including humans, suffering from prostate cancer; and therapeutic agents effective for use in such methods. The therapeutic method of the invention will most commonly be used in the treatment of individuals with advanced prostate cancer.

Enhancement of castration-induced tumor cell death and delay of the progression of androgen-sensitive prostatic cancer cells to androgen-independent is achieved by inhibiting the expression of TRPM-2 by the cells. Experiments were performed in three model systems, the in vivo Shionogi tumor model, the human TRPM-2 transfected LNCaP model, and the human PC-3 model, which taken together demonstrated that such inhibition leading to delay of androgen-independence can be achieved by treating androgen-sensitive prostatic tumor cells with antisense oligodeoxynucleotides (ODNs).

In the first experiment, the ability of a mouse TRPM-2 antisense molecule, ( Seq. ID. No. 1) to delay onset of androgen independence in the Shionogi tumor model was evaluated. The Shionogi tumor model is a xenograft of an androgen-dependent mouse mammary carcinoma that grows subcutaneously in male syngeneric hosts. Shionogi tumor cells are highly tumorigenic and locally invasive. The cells have been shown to respond to androgen withdrawal in a manner which mimics the observed behavior of prostatic tumor cells, and have been accepted as a valid model for prostate cancer in humans. (Bruchovsky et al., *Cancer Res.* 50:2275-2282 (1990); Rennie et al., *Cancer Res.* 48:6309-6312 (1988); Bruchovsky et al., *Cell* 13:272-280 (1978); Gleave et al., in *Genitourinary Oncology*, pp. 367-378, Lange et al., eds, Lippencott (1997); Gleave et al., *J. Urol.* 157:1727-1730 (1997); Bruchovsky et al., *The Prostate* 6:13-21 (1996)). Thus, androgen withdrawal precipitates apoptosis and tumor regression in a highly reproducible manner. Further, changes in expression of TRPM-2 and Bcl-2 in human prostate cancer following castration and during progression to androgen independence are similar to those observed in Shionogi tumor cells. Thus, the Shionogi tumor model mimics many of the characteristics of prostate cancer cells. Further, the Shionogi tumor model provides a very useful model for the evaluation of the ability of compounds to delay the onset of androgen-independence. Despite complete tumor regression after castration, rapidly growing androgen-independent Shionogi tumors invariably recur after one month, which provides a reliable end point to evaluate agents which can delay the progression to androgen-independence. In general, events which occur in the Shionogi tumor model within one month occur in human patients within about two years.

The ability of the antisense ODNs that inhibit expression of TRPM-2 to delay the onset of androgen-independence was evaluated by measuring tumor volume post-castration in the Shionogi tumor model. The test animals (n=7) were treated intraperitoneally once daily with 12.5 mg/kg repeat doses of antisense TRPM-2 ODNs (Seq. ID. No. 1) in a buffered saline solution. As a control, animals (n=7) were treated with a mismatch ODN (Seq. ID. No. 2). As shown in FIG. 1, both test and control groups showed the expected decline in tumor volume immediately following castration, but the tumors in the antisense TRPM-2 ODN-treated mice regressed faster than the controls. The control group also exhibited the expected increase in tumor volume which is associated the development of androgen-independence. In contrast, at 49 days post-castration, little tumor regrowth had occurred in the mice treated using the antisense TRPM-2 ODN. Tumors did eventually recur in the antisense TRPM-2 ODN-treated mice, but the median time to recurrence is approximately twice that of the control group. Thus, inhibition of TRPM-2 is effective not only for increasing the amount of cell death which occurs immediately following androgen withdrawal, but also for delaying the onset of androgen-independence. The more rapid decrease in tumor volume in the mice treated with antisense TRPM-2 ODNs was due to earlier onset and more extensive castration-induced apoptosis. This was confirmed by detecting poly(ADP-ribose) polymerase (PARP) cleavage fragments in Shionogi tumor specimens (Miyake, et al., *Cancer Res.* 60:170-176 (2000)).

Figure 2:
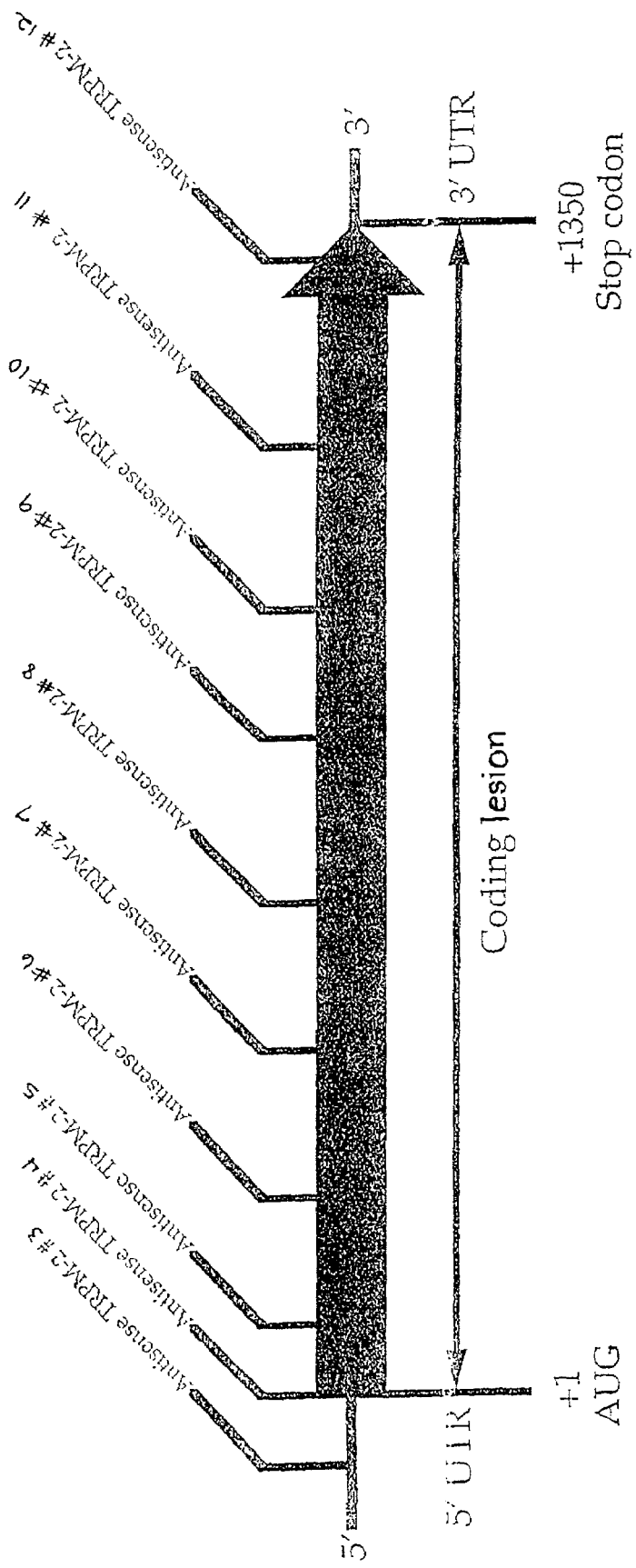
FIG. 2 shows the positions of 10 antisense oligonucleotides evaluated for the ability to inhibit TRPM-2 expression and delay onset of androgen-independence.
Figure 3:
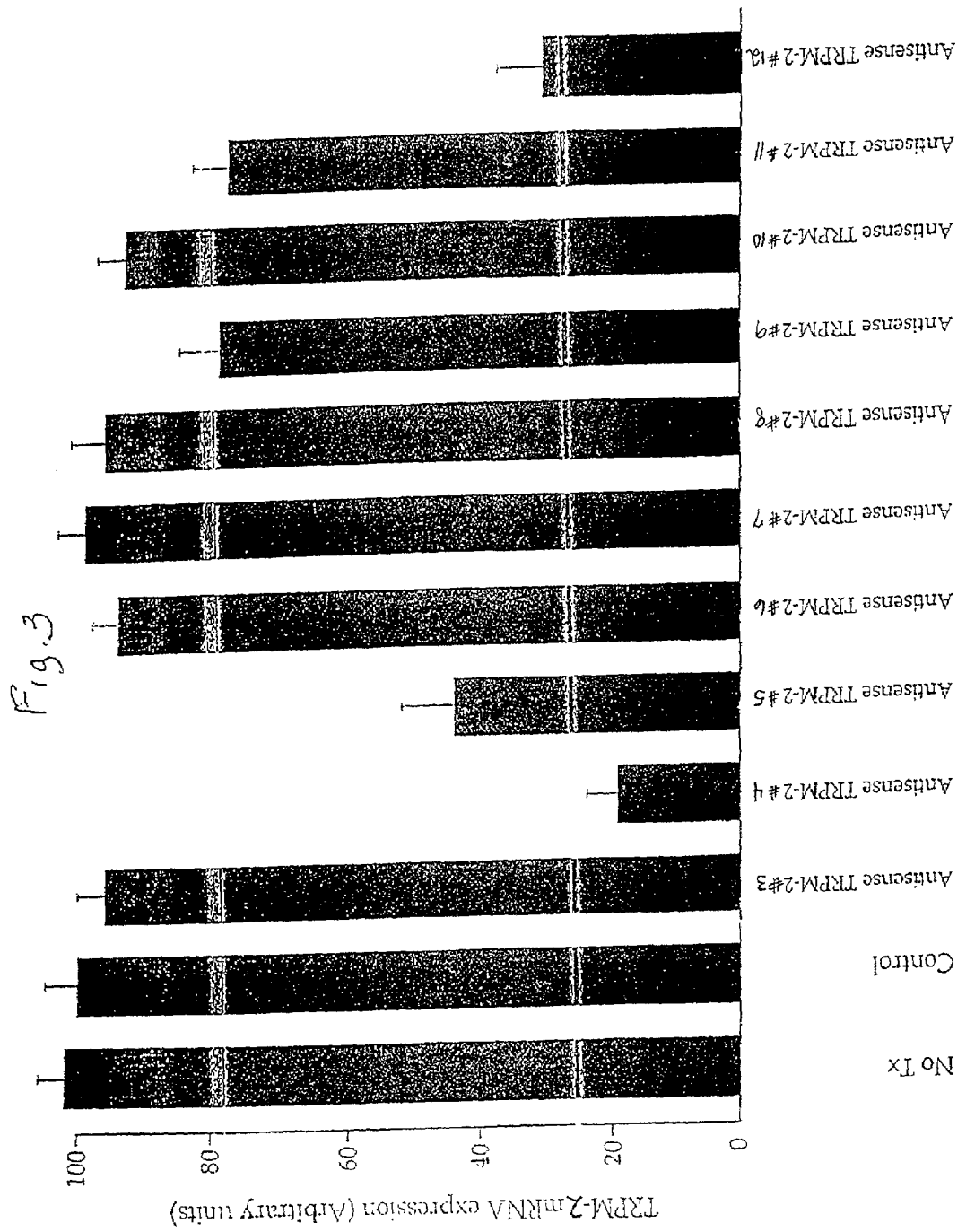
FIG. 3 shows expression levels of TRPM-2 mRNA in the presence of various antisense ODNs.

To evaluate which human antisense ODNs complementary to TRPM-2 mRNA sequences are most effective for this purpose, a series of ten antisense phosphorothioate ODNs were prepared spanning various mRNA regions as shown in FIG. 2. The sequences of these ten ODNs are set forth in the attached Sequence Listing as Seq. ID. Nos. 3-12. The ten human antisense ODNs were evaluated using TRPM-2 transfected LNCaP cells and human prostate cancer PC-3 cells for their ability to inhibit expression of TRPM-2 mRNA. As shown in FIG. 3, the antisense ODNs tested produced variable levels of inhibition of TRPM-2 mRNA expression, with the best results being achieved with Seq. ID Nos. 4, 5, and 12. Sequence ID No. 5 corresponds to the sequence used by Sensibar et al. that produced inhibition of TRPM-2 expression LNCaP cells, and is complementary to the first 21 bases of the TRPM-2 mRNA. The most effective down regulation occurred with Seq. ID No. 4. Common to all of the effective sequences is an overlap with either the initiation or termination sites of the TRPM-2 mRNA. Thus, in a general sense, the method of the invention can be practiced with antisense oligonucleotides which are complementary to a region of the TRPM-2 mRNA spanning either the translation initiation site or the termination site.

In accordance with a further aspect of with the invention, therapeutic treatment of individuals, including human individuals, suffering from prostate cancer is achieved by initiating androgen-withdrawal to induce apoptotic cell death of prostatic tumor cells in the individual, and administering to the individual a composition effective to inhibit expression of TRPM-2 by the tumor cells, thereby delaying the progression of prostatic tumor cells to an androgen-independent state in an individual.

Initiation of androgen withdrawal may be accomplished via surgical (removal of both testicles) or medical (drug-induced suppression of testosterone) castration, which is currently indicated for treatment of prostate cancer. Medical castration can be achieved by various regimens, including LHRH agents or antiandrogens. (Gleave et al., *CMAJ* 160: 225-232 (1999)). Intermittent therapy in which reversible androgen withdrawal is effected is described in Gleave et al. *Eur. Urol.* 34 (Supp. 3): 37-41 (1998).

The inhibition of TRPM-2 expression may be transient, and ideally should occur coincident with androgen withdrawal. In humans, this means that inhibition of expression should be effective starting within a day or two of androgen withdrawal and extending for about 3 to 6 months. This may require multiple doses to accomplish. It will be appreciated, however, that the period of time may be more prolonged, starting before castration and expending for substantial time afterwards without departing from the scope of the invention.

Antisense TRPM-2 ODNs have also been determined to enhance chemosensitivity in human renal cell cancer (RCC). RCC is a chemoresistant disease with no active chemotherapeutic agent with objective response rates higher than 10%. Increased TRPM-2 expression in renal proximal convoluted cells undergoing apoptosis has been observed after various stimuli including unreteral obstruction and aminoglycosides. However, functional significance of TRPM-2 expression in RCC has not been well documented. Test results show, however, that antisense TRPM-2 ODN enhances chemosensitivity in human RCC CaKi-2 cells (See Example 6, infra).

Figure 8:
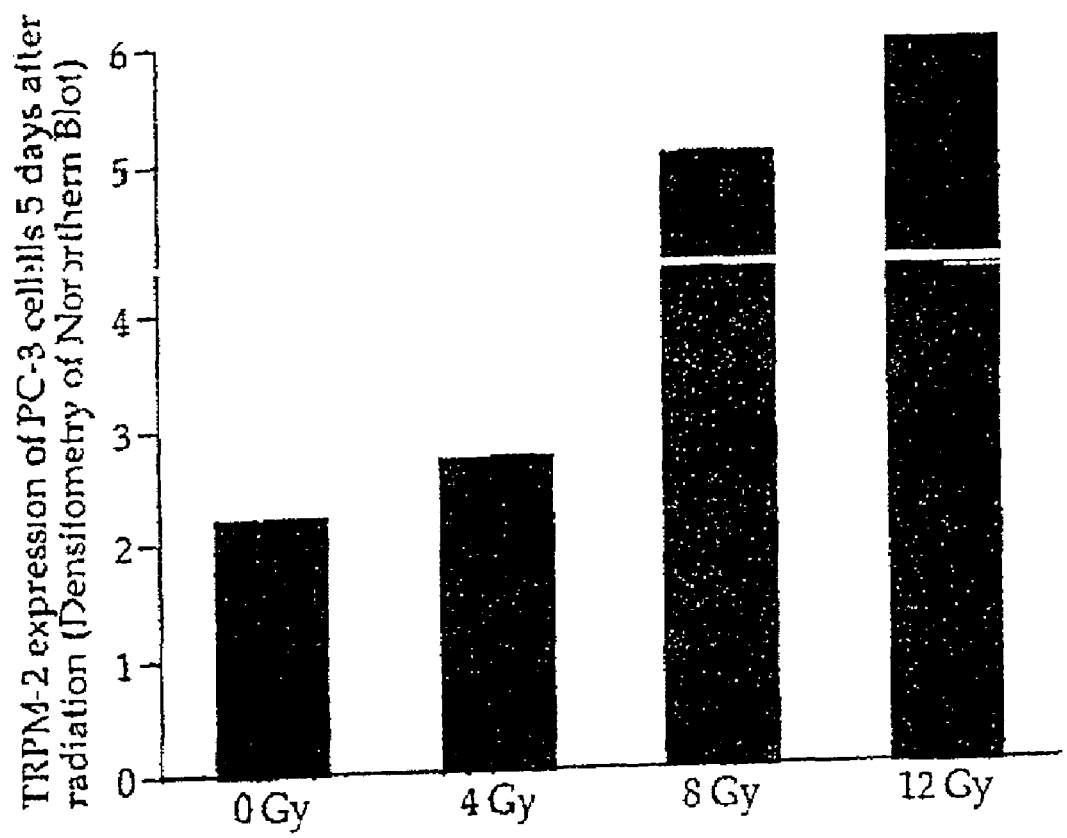
FIG. 8 shows TRPM-2 expression in PC-3 prostate cancer cells after various doses of radiation.

Antisense TRPM-2 ODNs were also found to increase sensitivity to radiation (See Example 7 and FIG. 8).

Inhibition of expression of TRPM-2 may be accomplished by the administration of antisense ODNs, particularly antisense ODNs which are complementary to a region of the TRPM-2 mRNA spanning either the translation initiation site or the termination site. For treatment of prostate cancer in humans, specific useful sequences are those shown in Seq. ID Nos. 4, 5 and 12.

The ODNs employed may be modified to increase the stability of the ODN in vivo. For example, the ODNs may be employed as phosphorothioate derivatives (replacement of a non-bridging phosphoryl oxygen atoms with a sulfur atom) which have increased resistance to nuclease digestion. MOE modification (ISIS backbone) is also effective.

Administration of antisense ODNs can be carried out using the various mechanisms known in the art, including naked administration and administration in pharmaceutically acceptable lipid carriers. For example, lipid carriers for antisense delivery are disclosed in U.S. Pat. Nos. 5,855,911 and 5,417,978 which are incorporated herein by reference. In general, the antisense is administered by intravenous, intraperitoneal, subcutaneous or oral routes, or direct local tumor injection. From the experiments performed using the Shionogi mouse model, it appears that the antisense ODN is preferentially active in the tumor cells. Indeed, TRPM-2 expression in non-tumor tissues was substantially unaffected, and no side effects of the antisense ODN administration were observed.

The amount of antisense ODN administered is one effective to inhibit the expression of TRPM-2 in prostatic cells. It will be appreciated that this amount will vary both with the effectiveness of the antisense ODN employed, and with the nature of any carrier used. The determination of appropriate amounts for any given composition is within the skill in the art, through standard series of tests designed to assess appropriate therapeutic levels.

The method for treating prostate cancer in accordance with the invention may further include administration of chemotherapy agents and/or additional antisense ODNs directed at different targets. For example, it has been found using the Shionogi tumor model that antisense TRPM-2 ODN increases sensitivity to conventional chemotherapy agents such as taxanes (paclitaxel or docetaxel) and mitoxanthrone (FIGS. 12A and 12B). As shown in FIGS. 12A and 12B, treatment with antisense TRPM-2 ODN in the presence of taxol or mitoxanthrone resulted in a reduced tumor volume as compared to the combination of taxol or mitoxanthrone with the mismatch (MM) ODN. Other agents likely to show synergistic activity include other cytotoxic agents (e.g. cyclophosphamide, topoisomerase inhibitors), angiogenesis inhibitors, differentiation agents and signal transduction inhibitors. Similarly, combinations of TRPM-2 antisense with other antisense species such as antisense Bcl-2 ODN worked better at killing Shionogi cells in vitro than either ODN alone. Thus, TRPM-2 can work in concert with other antisense molecules, such as antisense Bcl-2, Bcl-xl and c-myc ODN to provide greater effectiveness.

The invention will now be further described with reference to the following, non-limiting examples.

EXAMPLE 1

Shionogi tumor model experiments were performed using cells from the Toronto subline of transplantable SC-115 AD mouse mammary carcinoma. For in vivo studies, approximately $5 \times 10^6$ cells of the Shionogi carcinoma were injected subcutaneously in adult male DD/S strain mice. When the Shionogi tumors became 1 to 2 cm in diameter, usually 2 to 3 week after injection, castration was performed through an abdominal incision under methoxyflurane anesthesia. Details of the maintenance of mice, tumor stock and operative procedures have been previously described. Bruchovsky et al., *Cancer res.* 50:2275-2282 (1990); Rennie et al., *Cancer Res.* 48:6309-6312 (1988); Bruchovsky et al., *Cell* 13:272-280 (1978); Gleave et al., in *Genitourinary Oncology*, pp. 367-378, Lange et al., eds, Lippencott (1997); Gleave et al., *J. Urol.* 157:1727-1730 (1997); Bruchovsky et al., *The Prostate* 6:13-21 (1996)).

Mice were randomly selected for treatment with murine phosphorothioate antisense TRPM-2 ODN (Seq. ID No. 1) or a mismatch control (Seq. ID No. 2) which is two bases different in sequence from the antisense TRPM-2 ODN. Each experimental group consisted of 7 mice. One day after castration, 12.5 mg/kg of antisense TRPM-2 or mismatch control ODN dissolved in phosphate buffered saline were injected intraperitoneally once daily into each mouse of 40 days. Tumor volume was measured twice weekly, and calculated by the formula length×width×depth×0.5236. Gleave et al., *Cancer Res.* 52:1598-1605 (1992). Data points were reported as average tumor volumes±standard deviation.

The results of this study are shown in FIG. 1. As shown, Shionogi tumors regressed faster and complete regression occurred earlier in mice treated with antisense TRPM-2 ODN. Furthermore, treatment with antisense TRPM-2 ODN substantially delayed the onset of androgen-independence which is reflected by the increase in tumor volume after day 21 in the control animals. No side effects associated with antisense TRPM-2 or the mismatch control were observed.

To examine the effects of in vivo ODN treatment on levels of TRPM-2 mRNA, Northern blot analysis was performed on Shionogi tumor tissue from mice. The mice were treated daily with 12.5 mg/kg of antisense TRPM-2 ODN (n=6) or the mismatch control (n=6) by intraperitoneal injection starting one day after castration. On the fourth day after castration, tumor tissues were harvested and analyzed by Northern blot for TRPM-2 mRNA. Antisense TRPM-2 ODN resulted in a 75% reduction in TRPM-2 mRNA llevels in Shionogi tumors compared to mismatch control ODN treated tumors. (FIG. 3).

Comparable analyses were performed on normal mouse organs. Samples of spleen, kidney, prostate and brain were harvested from Shionogi tumor mice treated with antisense TRPM-2 ODN and mismatch control under the same treatment schedule, and analyzed by Northern blot. Although TRPM-2 mRNA levels was significantly lower in tumor tissues, antisense TRPM-2 ODN had no effect on TRPM-2 mRNA levels in the normal organs.

EXAMPLE 2

The sequence selectivity of the antisense TRPM-2 ODN (Seq. ID. No. 1) was confirmed by comparing expression levels of TRPM-2 mRNA in Shionogi tumor cells maintained in vitro, after treatment with the varying levels of antisense TRPM-2 ODN or a mismatch control (Seq. ID. No. 2). To facilitate uptake of the ODNs into the cells, the ODNs were formulated in a cationic lipid carrier (Lipofectin™, (Life Technologies, Inc.)). Cells were treated twice over a period of two days using the following protocol. Cells were preincubated for 20 minutes with 4 µg/ml of lipofectin in serum free OPTI-MEM™ (Life Technologies, Inc.) and then incubated with the medium containing the selected concentration of ODN and lipofectin for four hours. The medium was then replaced with the standard culture medium.

Figure 4:
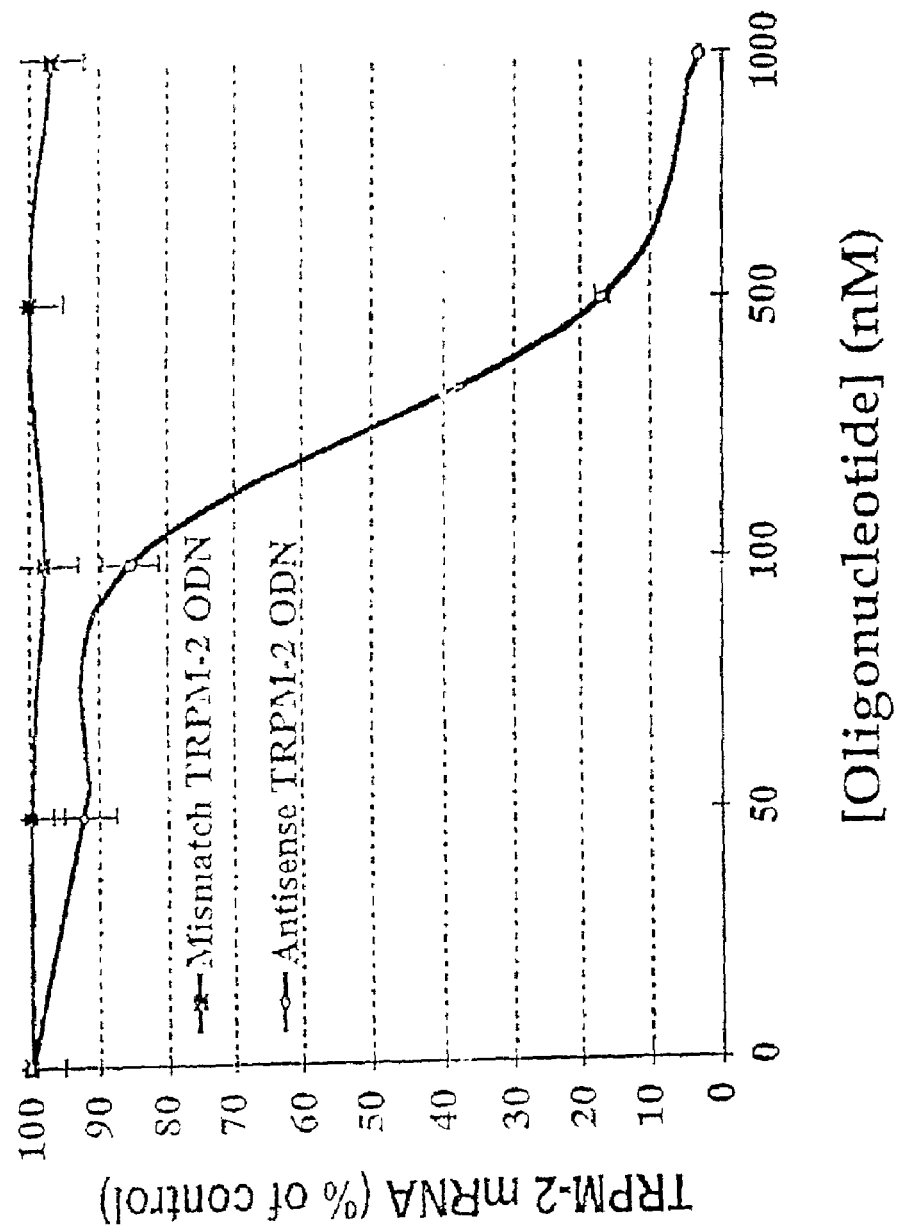
FIG. 4 shows the levels of TRPM-2 mRNA in Shionogi cells treated in vitro with varying amounts of antisense TRPM-2 ODN or a mismatch control.

The amount of TRPM-2 mRNA in the cells was evaluated using Northern blot analysis. As shown in FIG. 4, treatment of Shionogi cells with antisense TRPM-2 ODN reduced TRPM-2 mRNA levels in a dose dependent manner. In contrast, TRPM-2 mRNA levels were not affected by the mismatch ODN (Seq. ID. No. 2) at any of the employed concentrations. Thus, the affect of antisense TRPM-2 ODN is apparently sequence specific.

EXAMPLE 3

Figure 5:
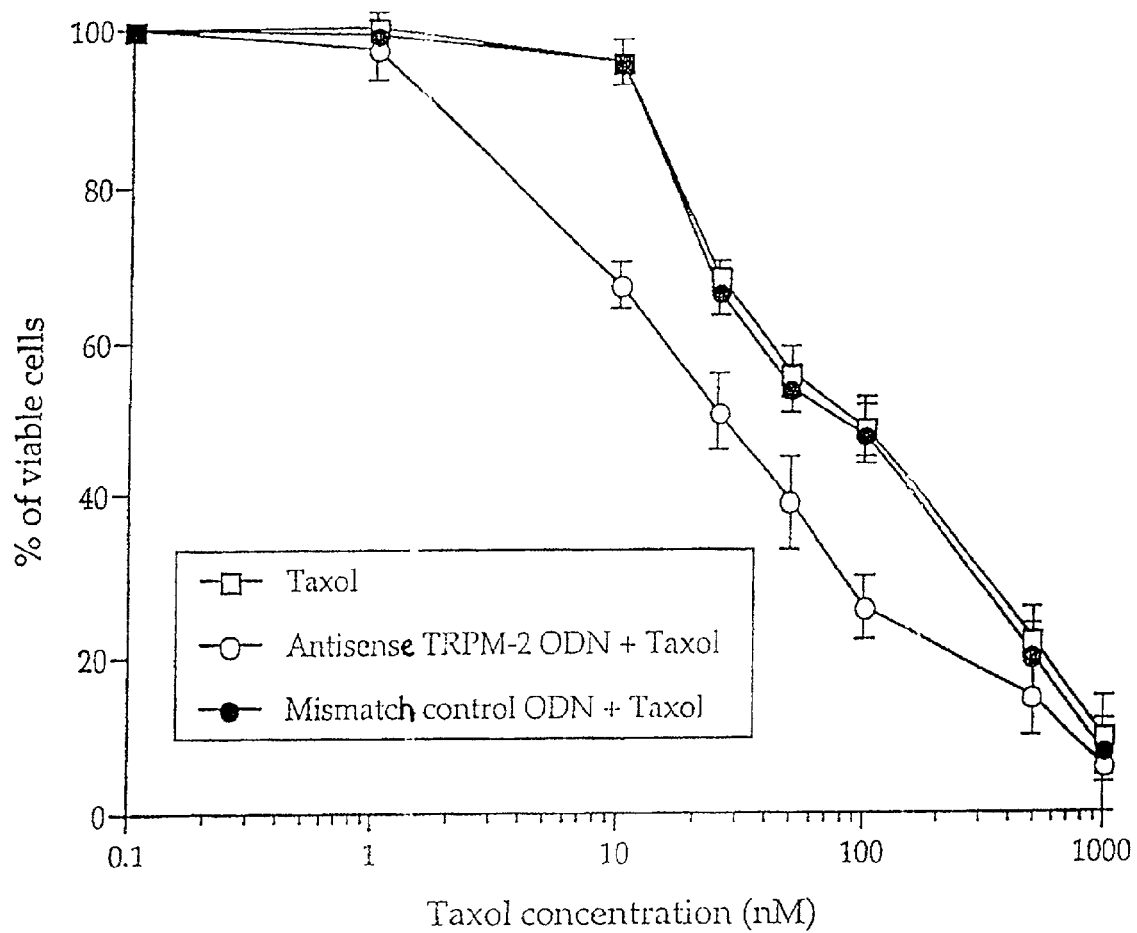
FIG. 5 shows the dose-response curve for combinations of taxol and antisense TRPM-2 ODN.

Shionogi cells maintained in vitro were treated with varying amounts of taxol alone or in combination with 500 nM antisense TRPM-2 ODN (Seq. ID. No. 1) or the mismatch control (Seq. ID No. 2). The cells were treated twice, as described in Example 2, and the percentage of viable cells remaining was determined. The results are summarized in FIG. 5. As shown, the inclusion of antisense TRPM-2 ODN shifted the dose-response curve to the left, lowering the $IC_{50}$ by a factor of 5 to 10. Similar results were achieved using mitoxanthrone in place of paclitaxel (FIGS. 12A and 12B).

EXAMPLE 4

Figure 6:
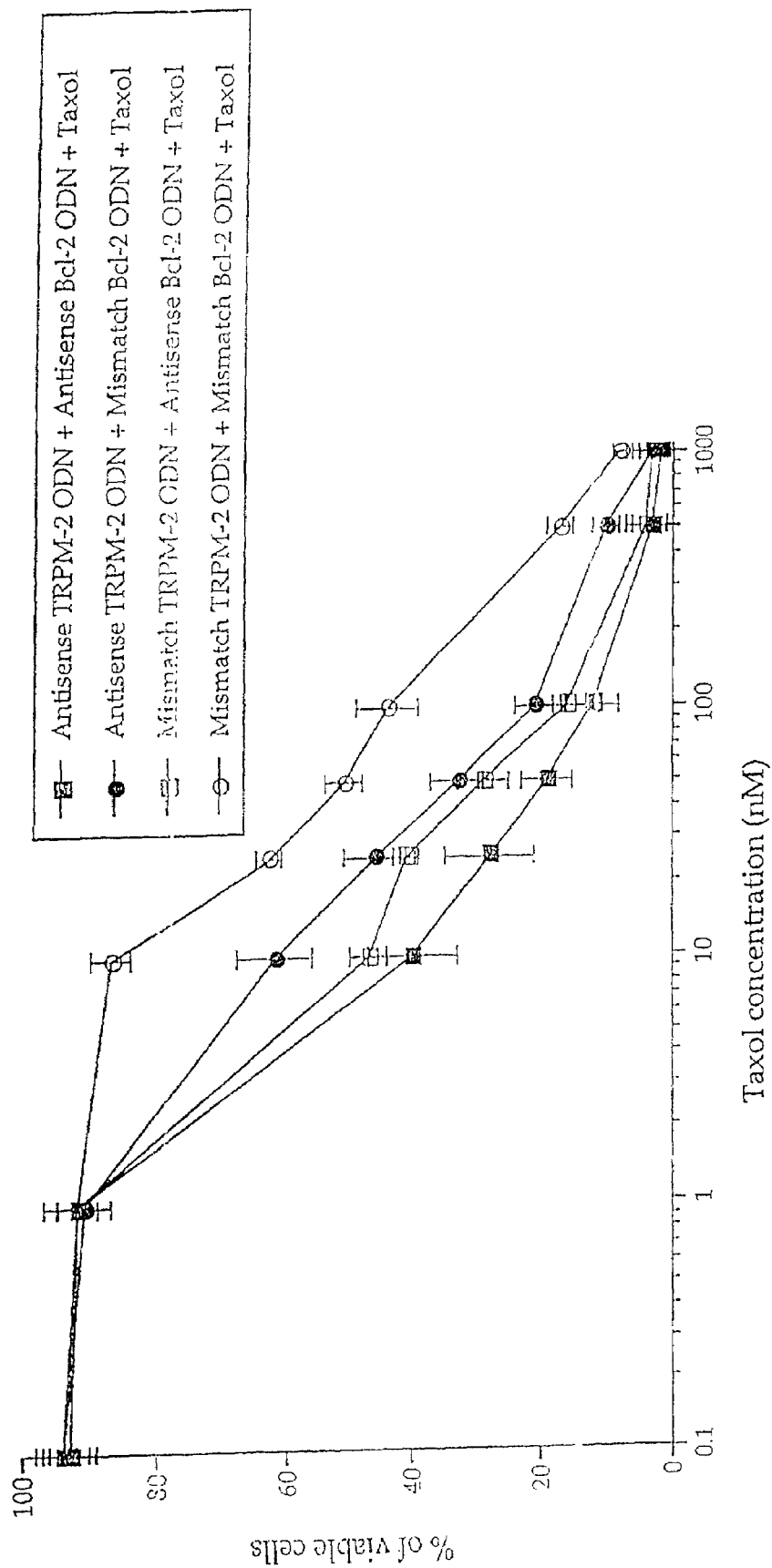
FIG. 6 shows the dose-response curve for combinations of taxol, antisense TRPM-2 ODN and antisense Bcl-2 ODN.

The experiment of Example 3 was repeated, with the addition of antisense Bcl-2 ODN (Seq. ID. No. 13) or a mismatch Bcl-2 ODN (Seq. ID. No. 14) in various combinations with antisense/mismatch TRPM-2 ODN and taxol. The results are shown in FIG. 6. The combination of antisense TRPM-2 ODN with antisense Bcl-2 ODN and taxol further enhanced the cytotoxic effects of taxol. Thus, the targeting of additional anti-apoptotic agents appears to provide therapeutic benefits.

EXAMPLE 5

To identify appropriate antisense TRPM-2 ODN sequences for use in human therapy, antisense ODN sequences directed against 10 different sites of the human TRPM-2 gene (FIG. 2, Seq. ID Nos. 3-12) were synthesized and tested for their ability to decrease TRPM-2 gene expression in human prostate cancer PC-3 and transfected LNCaP cells that overexpress TRPM-2 using the same treatment protocol described in Example 2. The results are summarized in FIG. 3. As shown, sequences 4, 5 and 12 are active for reduction of TRPM-2 expression. These three sequences overlap or are immediately adjacent to the translation initiation or termination sites.

EXAMPLE 6

Immunohistochemical staining was used to characterize clusterin expression in 17 RCC and normal kidney tissues obtained from radical nephrectomy specimens. TRPM-2 expression in human renal cancer cell lines ACHN, CaKi-1 and CaKi-2 was evaluated by Northern and Western blot analyses. Northern blot analysis was used to assess changes in TRPM-2 mRNA expression after antisense TRPM-2 ODN treatment. The effects of combined antisense TRPM-2 ODN and taxol treatment on CaKi-2 cell growth was examined using a MTT assay.

Figure 7A:
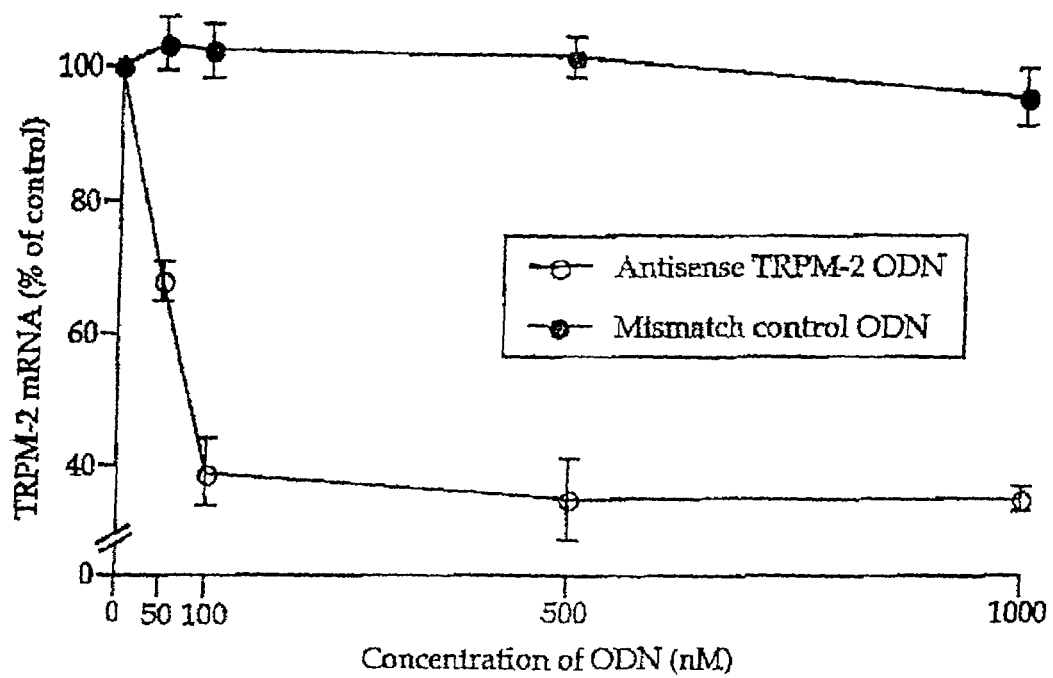
FIG. 7A shows decease in TRPM-2 mRNA levels in human renal cell cancer after treatment with antisense TRPM-2 ODNs.
Figure 7B:
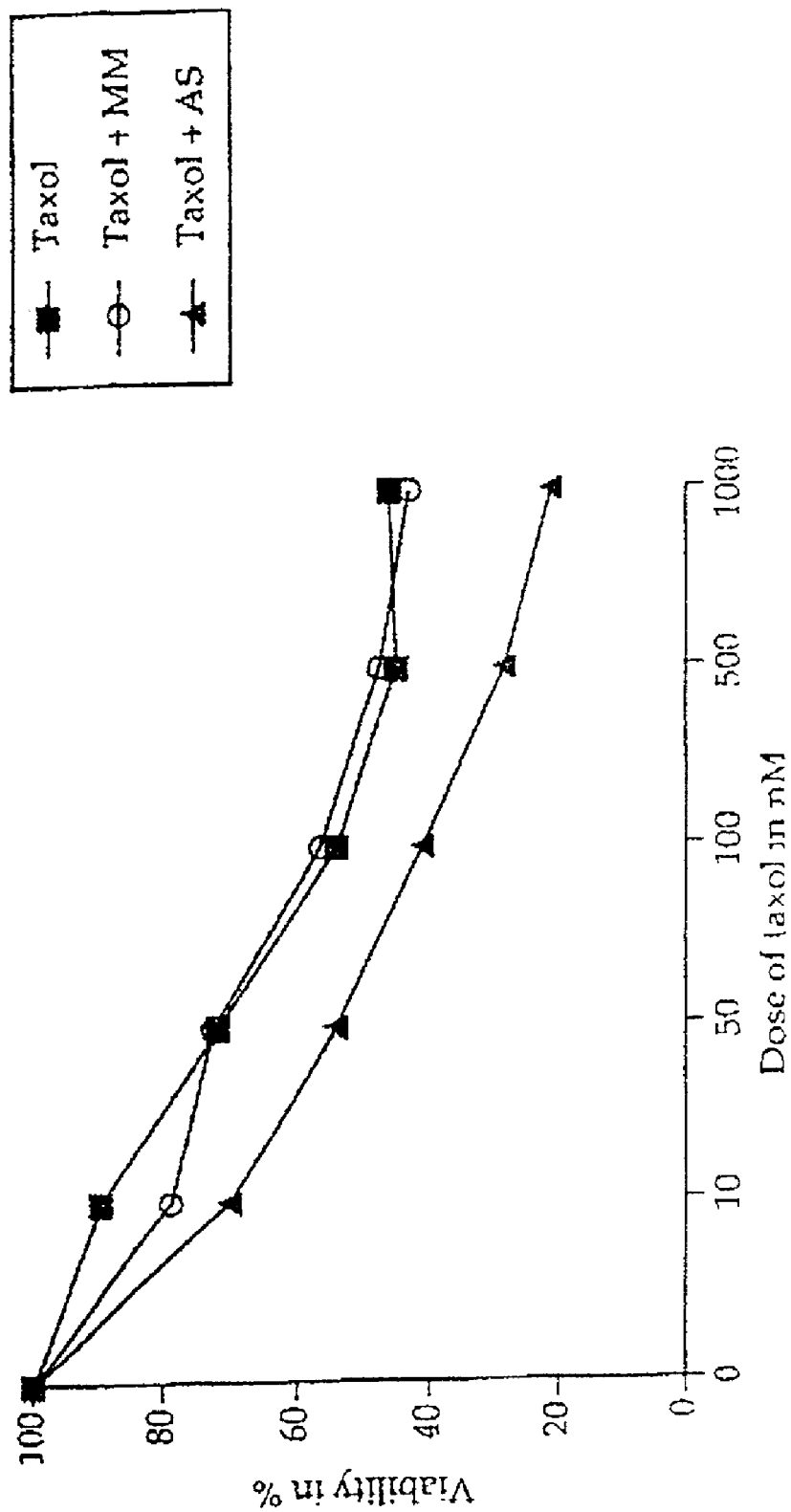
FIG. 7B shows the increase in chemosensitivity of human renal cell cancer to taxol after treatment with antisense TRPM-2 ODNs.

Immunostaining showed an increased clusterin expression in 11 RCC specimens in comparison to the adjacent normal kidney tissue. In the remaining 6 cases, no difference was seen between malignant and normal tissue. Both TRPM-2 mRNA and protein expression were detectable in all three human RCC cell lines, with highest levels for CaKi-2. Antisense TRPM-2 ODN (Seq. ID. No. 1), but not mismatch control ODN (Seq. ID. No. 2), inhibited TRPM-2 expression in CaKi-2 cells in a dose dependant and sequence specific manner (FIG. 7A). Furthermore, antisense TRPM-2 ODN substantially enhanced taxol chemosensitivity, reducing IC50 of taxol by 1 log (500 nM to 50 nM) compared to mismatch control ODN (FIG. 7B). These data demonstrate that TRPM-2 and its protein, clusterin, are expressed at higher levels in RCC compared to normal kidney tissue, and that antisense TRPM-2 ODN may be useful in enhancing the cytotoxic effects of conventional chemotherapy in advanced RCC.

EXAMPLE 7

Figure 9A:
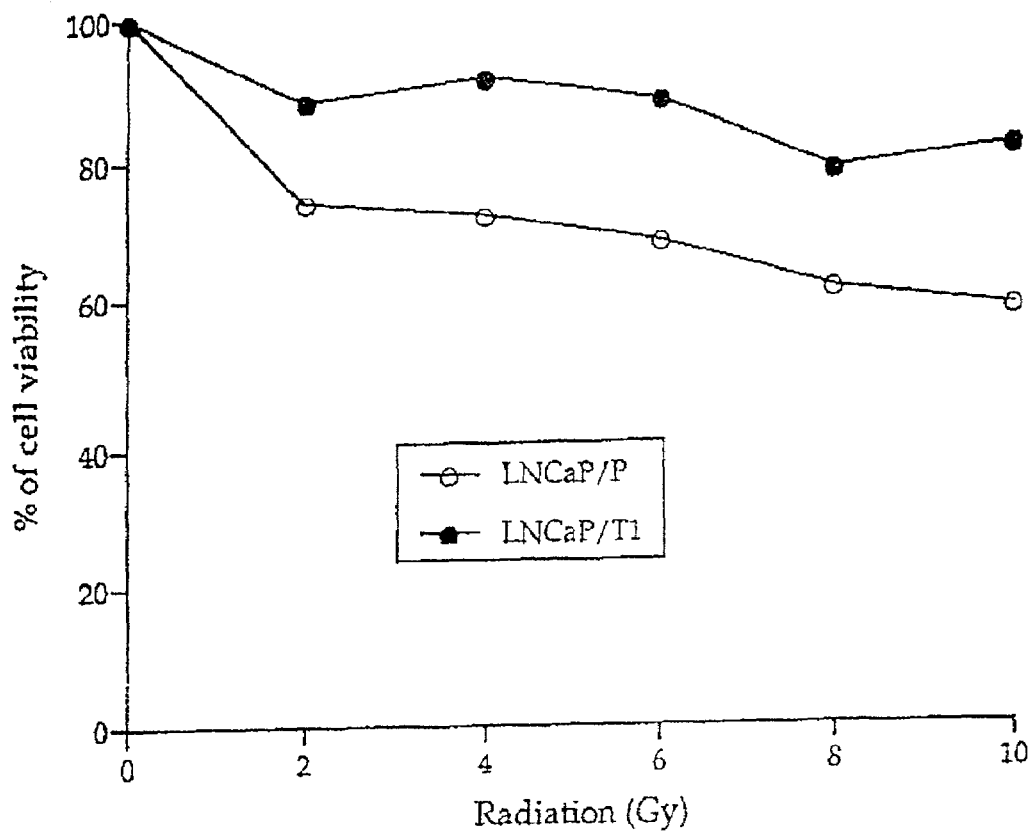
FIGS. 9A and 9B show the comparative radiation resistance of human prostate cell lines which overexpress (LNCaP/T) and normally (LNCaP/P) express TRPM-2.
Figure 9:
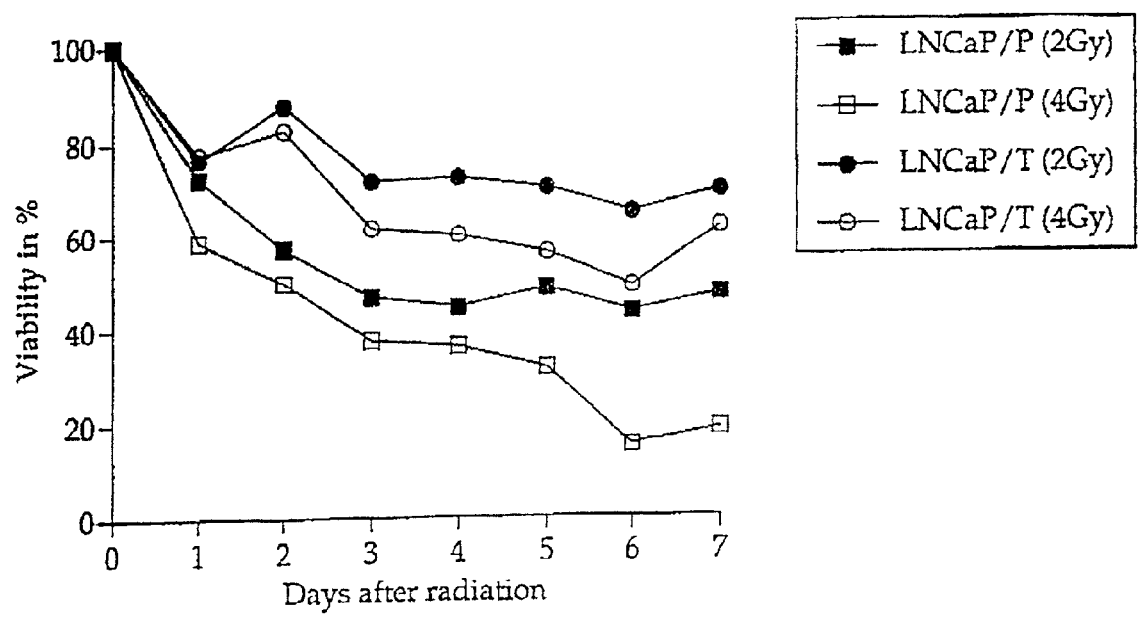
Figure 10:
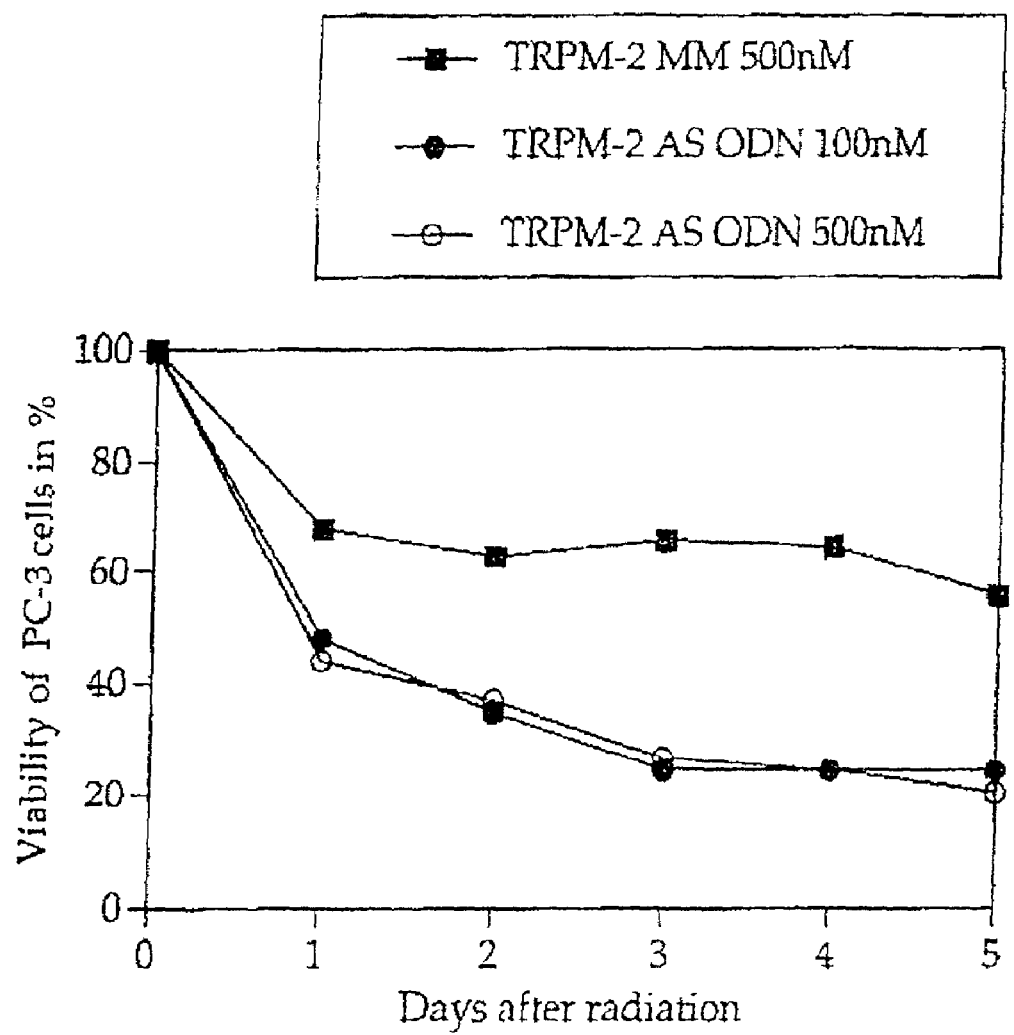
FIG. 10 shows the increased susceptibility of PC-3 cells to radiation after treatment with antisense TRPM-2 ODN.
Figure 11A:
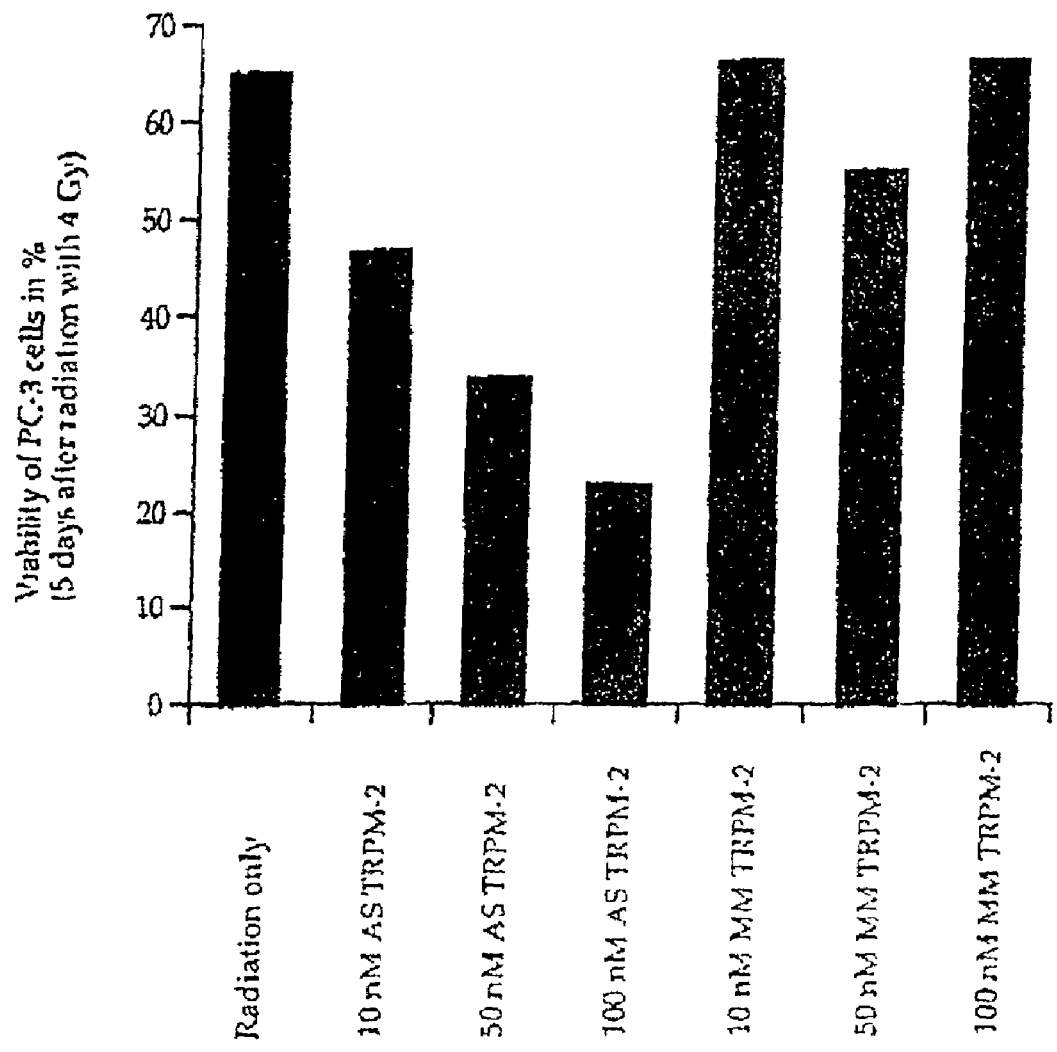
FIGS. 11A and 11B show the increased sensitivity of PC-3 cells to radiation after treatment with antisense TRPM-2 ODN.
Figure 11B:
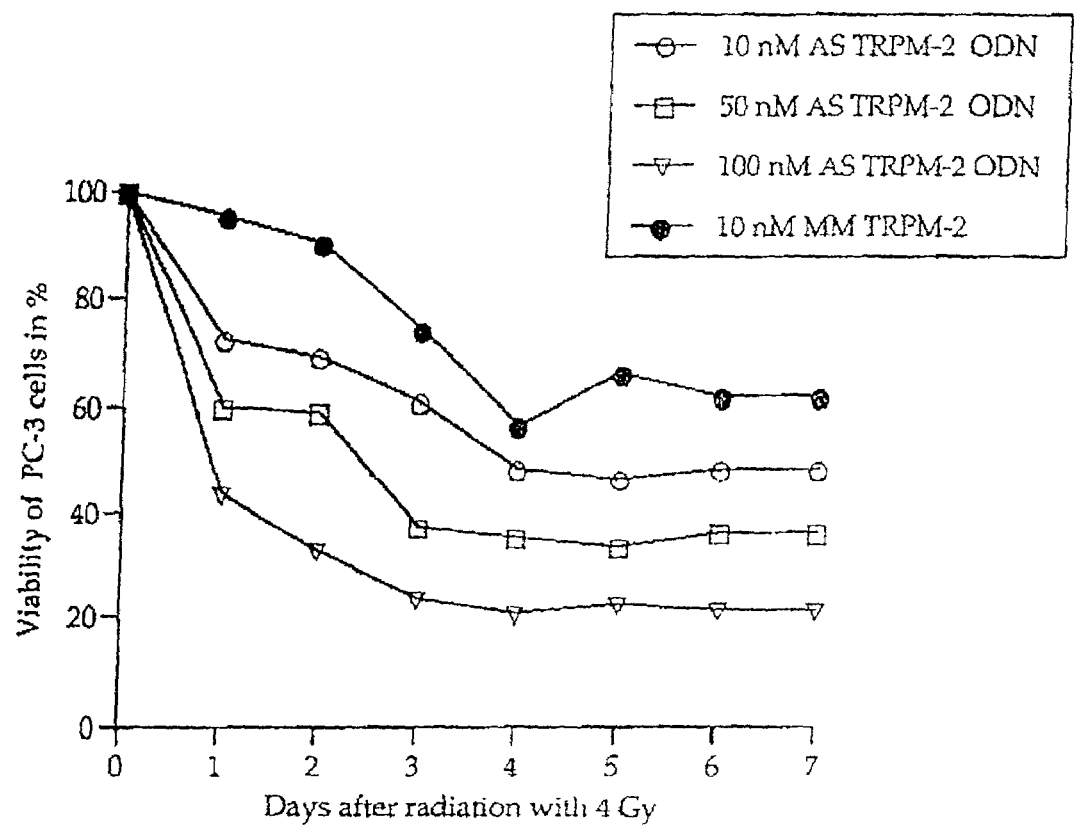
Figures 13A, 13B:
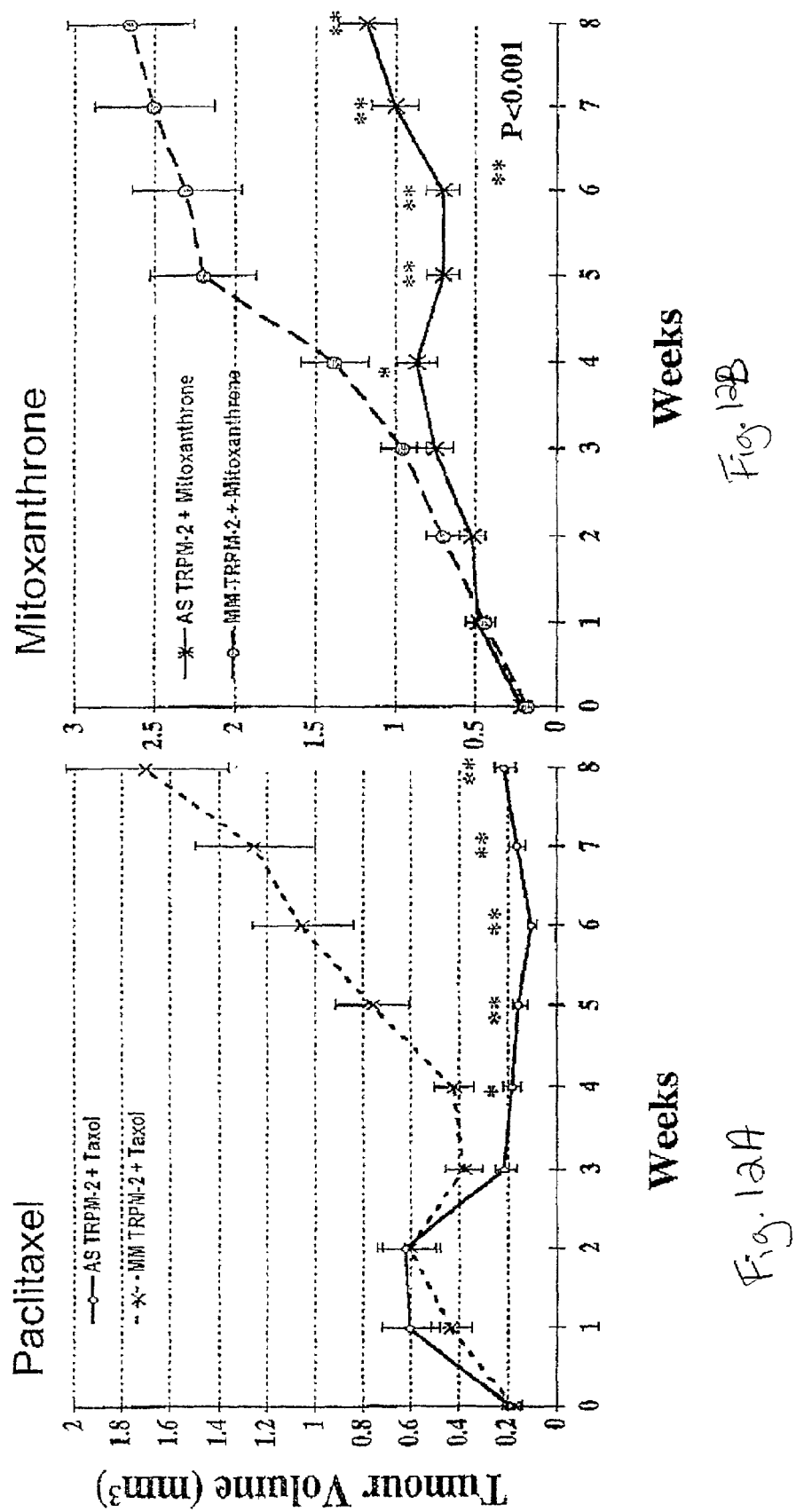

Antisense TRPM-2 ODNs enhance radiation sensitivity of cancer cells which express TRPM-2. Using northern analysis, we found that radiation therapy results in dose and time dependent increases in TRPM2 gene expression in human prostate cancer PC-3 cells (FIG. 8). Overexpression of TRPM2 results in increased resistance to radiation induced cell death. Human prostate LNCaP cells that overexpress TRPM2 (LNCaP/T1) are more resistant to radiation therapy (FIGS. 9A and B). Treatment of human prostate cancer PC-3 cells with 100 and 500 nM antisense TRPM-2 ODNs (Seq. ID. NO. 1) significantly reduces cell survival after a single treatment of 4 Gy radiation therapy compared to mismatch ODN (Seq. ID No. 2) treatment. (FIG. 10). FIGS. 11A and B show does dependent radiation sensitization of human prostate cancer PC-3 cells after treatment with 10, 50, and 100 nM antisense TRPM-2 oligo in vitro.

EXAMPLE 8

To determine whether treatment with human antisense TRPM-2 ODN enhances chemosensitivity in the PC3 human prostate cancer cell line, mice bearing PC3 tumors were treated with antisense human TRPM-2 ODN plus micellar paclitaxel or mitoxantrone, and mismatch control ODN plus micellar paclitaxel or mitoxantrone (FIGS. 12A and 12B). ODN was administered for 28 days and either 0.5 mg micellar taxol or 0.3 mg mitoxantrone were administered on two occasions: from day 10 to 14, and day 24 to 28. A significant reduction in tumor size was observed in the antisense ODN treated animals as compared to those treated with mismatch control ODN. This effect was even more pronounced after the second dosing of the micellar paclitaxel or mitoxantrone.

The invention claimed is:

1. A method for treating prostate cancer in an individual suffering from prostate cancer, comprising the steps of initiating androgen-withdrawal to induce apoptotic cell death of prostatic tumor cells in the individual, and administering to the individual a composition effective to inhibit expression of TRPM-2 by the tumor cells, thereby delaying the progression of prostatic tumor cells to an androgen-independent state in an individual, wherein the composition effective to inhibit expression of TRPM-2 is an antisense oligonucleotide that is complementary to a region of the TRPM-2 mRNA that is complementary to SEQ ID NO.: 4.

2. The method of claim 1, wherein the antisense oligonucleotide consists of the sequence given by SEQ ID No. 4.

3. The method of claim 2, further comprising the step of administering to the individual a chemotherapy agent.

4. The method of claim 2, further comprising the step of administering to the individual a second antisense oligodeoxynucleotide which inhibits expression of an anti-apoptotic protein other than TRPM-2.

5. A method for treating prostate cancer in an individual suffering from prostate cancer, comprising the steps of initiating androgen-withdrawal to induce apoptotic cell death of prostatic tumor cells in the individual, and administering to the individual a composition effective to inhibit expression of TRPM-2 by the tumor cells, thereby delaying the progression of prostatic tumor cells to an androgen-independent state in an individual, wherein the composition effective to inhibit expression of TRPM-2 is an antisense oligonucleotide that is complementary to a region of the TRPM-2 mRNA that is complementary to SEQ ID NO: 12.

6. The method of claim 5, wherein the antisense oligonucleotide consists of the sequence given by SEQ ID No. 12.

7. The method of claim 6, further comprising the step of administering to the individual a chemotherapy agent.

8. The method of claim 6, further comprising the step of administering to the individual a second antisense oligodeoxynucleotide which inhibits expression of an anti-apoptotic protein other than TRPM-2.

9. A method for treating prostate cancer in an individual suffering from prostate cancer, comprising the steps of administering to the individual a composition effective to inhibit expression of TRPM-2 by the tumor cells, and administering to the individual a chemotherapy agent, wherein the composition effective to inhibit expression of TRPM-2 is an antisense oligonucleotide comprising the sequence given by SEQ ID No. 4.

10. The method of claim 9, wherein the chemotherapy agent is a taxane or mitoxanthrone.

11. A method for treating prostate cancer in an individual suffering from prostate cancer, comprising the steps of administering to the individual a composition effective to inhibit expression of TRPM-2 by the tumor cells, and administering to the individual a chemotherapy agent, wherein the composition effective to inhibit expression of TRPM-2 is an antisense oligonucleotide comprising the sequence given by SEQ ID No. 12.

12. The method of claim 11, wherein the chemotherapy agent is a taxane or mitoxanthrone.

* * * * *

SEQUENCE LISTING

```
<160> NUMBER OF SEQ ID NOS: 14

<210> SEQ ID NO 1
<211> LENGTH: 21
<212> TYPE: DNA
<213> ORGANISM: Murine
<220> FEATURE:
<223> OTHER INFORMATION: antisense TRPM-2 ODN

<400> SEQUENCE: 1
gcacagcagg agaatcttca t                                              21

<210> SEQ ID NO 2
<211> LENGTH: 21
<212> TYPE: DNA
<213> ORGANISM: Murine
<220> FEATURE:
<223> OTHER INFORMATION: mismatch control

<400> SEQUENCE: 2
gcacagcagc aggatcttca t                                              21

<210> SEQ ID NO 3
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 3
tggagtcttt gcacgcctcg g                                              21

<210> SEQ ID NO 4
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 4
cagcagcaga gtcttcatca t                                              21

<210> SEQ ID NO 5
```

```
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 5
attgtctgag accgtctggt c                                              21

<210> SEQ ID NO 6
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 6
ccttcagctt tgtctctgat t                                              21

<210> SEQ ID NO 7
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 7
agcagggagt cgatgcggtc a                                              21

<210> SEQ ID NO 8
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 8
atcaagctgc ggacgatgcg g                                              21

<210> SEQ ID NO 9
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 9
gcaggcagcc cgtggagttg t                                              21

<210> SEQ ID NO 10
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 10
ttcagctgct ccagcaagga g                                              21

<210> SEQ ID NO 11
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 11
```

```
aatttagggt tcttcctgga g                                                    21

<210> SEQ ID NO 12
<211> LENGTH: 21
<212> TYPE: DNA
<213> ORGANISM: HUMAN
<220> FEATURE:
<223> OTHER INFORMATION: antisense TRPM-2 ODN

<400> SEQUENCE: 12
gctgggcgga gttgggggcc t                                                    21

<210> SEQ ID NO 13
<211> LENGTH: 18
<212> TYPE: DNA
<213> ORGANISM: Murine
<220> FEATURE:
<223> OTHER INFORMATION: antisense Bcl-2 ODN

<400> SEQUENCE: 13
tctcccggct tgcgccat                                                        18

<210> SEQ ID NO 14
<211> LENGTH: 18
<212> TYPE: DNA
<213> ORGANISM: Murine
<220> FEATURE:
<223> OTHER INFORMATION: mismatch Bcl-2 ODN

<400> SEQUENCE: 14
tctcccggca tggtgcat                                                        18
```